(12) United States Patent
Agrawal et al.

(10) Patent No.: US 7,810,142 B2
(45) Date of Patent: Oct. 5, 2010

(54) AUDITING COMPLIANCE WITH A HIPPOCRATIC DATABASE

(75) Inventors: Rakesh Agrawal, San Jose, CA (US); Roberto Bayardo, Morgan Hill, CA (US); Christos Faloutsos, Pittsburgh, PA (US); Gerald George Kiernan, San Jose, CA (US); Ralf Rantzau, San Jose, CA (US); Ramakrishnan Srikant, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 1592 days.

(21) Appl. No.: 11/084,035

(22) Filed: Mar. 21, 2005

(65) Prior Publication Data

US 2006/0212491 A1 Sep. 21, 2006

(51) Int. Cl.
*H04L 9/00* (2006.01)
(52) U.S. Cl. .................................. 726/5; 707/608
(58) Field of Classification Search ................ 726/1–2, 726/6, 18, 22–26; 707/1, 3–5, 102, 103 R, 707/103 Z, 608–609, 648, 665, 667, 668, 707/673, 687, 690, 705–707, 713, 721, 731, 707/758–760, 763, 768–770, 802, 751, 754; 715/227, 249, 708, 336
See application file for complete search history.

(56) References Cited

U.S. PATENT DOCUMENTS

| | | | |
|---|---|---|---|
| 5,557,742 A | 9/1996 | Smaha et al. | 395/186 |
| 5,982,890 A | 11/1999 | Akatsu | 380/4 |
| 6,070,244 A | 5/2000 | Orchier et al. | 713/201 |
| 6,134,664 A | 10/2000 | Walker | 713/201 |
| 6,243,816 B1 * | 6/2001 | Fang et al. | 726/5 |
| 6,321,338 B1 * | 11/2001 | Porras et al. | 726/25 |
| 6,327,574 B1 | 12/2001 | Kramer et al. | 705/14 |
| 6,363,391 B1 * | 3/2002 | Rosensteel, Jr. | 707/102 |
| 6,405,318 B1 | 6/2002 | Rowland | 713/200 |
| 6,408,391 B1 * | 6/2002 | Huff et al. | 726/22 |
| 6,480,850 B1 | 11/2002 | Veldhuisen | 707/9 |
| 6,546,389 B1 | 4/2003 | Agrawal et al. | 707/6 |
| 6,585,778 B1 | 7/2003 | Hind et al. | 715/513 |
| 6,647,400 B1 * | 11/2003 | Moran | 707/205 |
| 6,668,325 B1 * | 12/2003 | Collberg et al. | 713/194 |
| 6,694,303 B1 | 2/2004 | Agrawal et al. | 706/52 |
| 6,757,699 B2 | 6/2004 | Lowry | 707/205 |

(Continued)

OTHER PUBLICATIONS

Agrawal et al., "Auditing Compliance with a Hippocratic Database," Proceedings of the 30th International Conference on Very Large Data Bases, Toronto Canada, Sep. 2004, 12pgs.

(Continued)

*Primary Examiner*—Kimyen Vu
*Assistant Examiner*—Leynna T Truvan
(74) *Attorney, Agent, or Firm*—IP Authority, LLC; Ramraj Soundararajan; Van Nguy

(57) ABSTRACT

An auditing framework for determining whether a database disclosure of information adhered to its data disclosure policies. Users formulate audit expressions to specify the (sensitive) data subject to disclosure review. An audit component accepts audit expressions and returns all queries (deemed "suspicious") that accessed the specified data during their execution.

18 Claims, 10 Drawing Sheets

U.S. PATENT DOCUMENTS

| | | | | |
|---|---|---|---|---|
| 6,804,787 | B2 | 10/2004 | Dick | 713/201 |
| 6,810,395 | B1* | 10/2004 | Bharat | 707/4 |
| 6,948,064 | B2* | 9/2005 | Smith et al. | 713/168 |
| 7,028,338 | B1* | 4/2006 | Norris et al. | 726/23 |
| 7,146,359 | B2* | 12/2006 | Castellanos | 707/5 |
| 7,167,892 | B2* | 1/2007 | Defosse et al. | 709/200 |
| 7,171,379 | B2* | 1/2007 | Menninger et al. | 705/28 |
| 7,284,274 | B1* | 10/2007 | Walls et al. | 726/25 |
| 7,296,155 | B1* | 11/2007 | Trostle et al. | 713/170 |
| 7,305,707 | B2* | 12/2007 | Mattsson | 726/22 |
| 7,315,826 | B1* | 1/2008 | Guheen et al. | 705/7 |
| 7,386,151 | B1* | 6/2008 | Moritz | 382/116 |
| 7,506,364 | B2* | 3/2009 | Vayman | 726/4 |
| 2001/0025346 | A1 | 9/2001 | Kayashima et al. | 713/200 |
| 2002/0178374 | A1 | 11/2002 | Swimmer et al. | 713/200 |
| 2004/0049693 | A1 | 3/2004 | Douglas | 713/200 |
| 2004/0111639 | A1 | 6/2004 | Schwartz et al. | 713/201 |
| 2004/0172558 | A1 | 9/2004 | Callahan et al. | 713/201 |

OTHER PUBLICATIONS

Agrawal et al., "Hippocratic Databases," Proceedings of the 28th International Conference on Very Large Data Bases, Hong Kong, China, Aug. 2002, 12 pgs.

Malvestuto et al., Computational Issues Connected with the Protection of Sensitive Statistics by Auditing Sum-Queries, Proceedings of the 10th International Conference on Scientific and Statistical Database Management, Capri, Italy, Jul. 1-3, 1998, pp. 134-144.

Jensen et al., "Incremental Implementation Model for Relational Databases with Transaction Time," IEEE Transactions on Knowledge and Data Engineering, V3, N4, Dec. 1991, pp. 461-473.

Lefevre et al., "Limiting Disclosure in Hippocratic Databases," Proceedings of the 30th International Conference on Very Large Data Bases, Toronto Canada, Sep. 2004, pp. 108-119.

Sellis, "Multiple-Query Optimization," ACM Transactions on Database Systems, V13, N1, Mar. 1988, pp. 23-52.

Chen et al. "NiagaraCQ: A Scalable Continuous Query System for Internet Databases," Proceedings of the 2000 ACM SIGMOD International Conference on Management of Data, Dallas, Texas, May 14-19, 2000, pp. 379-390.

Eswaran et al, "The Notions of Consistency and Predicate Locks in a Database System," Communications of the ACM, V19, N11, Nov. 1976, pp. 624-633.

Nanda et al., Oracle Privacy Security Auditing: Includes Federal Law Compliance with HIPAA, Sarbanes-Oxley & the Gramm-Leach-Bliley Act GLB, Rampant Techpress, Dec. 2003, pp. 574-578, 613-618.

Ryutov et al. "The Specification and Enforcement of Advanced Security Policies," Proceedings of the Third International Workshop on Policies for Distributed Systems and Networks, Monterey, California, Jun. 5-7, 2002, 11pgs.

*Database Management Systems*, McGraw-Hill, New York, USA, p. 229.

"The Platform for Privacy Preferences 1.0 (P3P1.0) Specification," <http://www.w3.org/TR/P3P/>, 130 pgs.

* cited by examiner

// Q is a simple selection query over a single table $T$, executed at time $\tau$.
// A is an audit expression over the same table $T$.

1) create an empty QGM for the audit query $AQ$
2) add $Q$ to $AQ$
3) add $A$ to $AQ$
4) rewrite $A$ to range over the result of $Q$ instead of $T$
5) replace $A$'s audit list with id($Q$)
6) replace $T$ with the view of $T^\tau$

Figure 2

1) create an empty QGM for the audit query $AQ$
2) add $Q$ to $AQ$
3) add $A$ to $AQ$
4) rewrite $A$ to additionally range over the result of $Q$ with quantifier $x$
5) for each quantifier $r$ in $A$ which is over a table $T$ also in $Q$
6)     substitute $x$ in place of $r$ in $A$
7) replace $A$'s audit list with $id(Q)$
8) replace every table $T_i$ referenced in $AQ$ with $T_i^\tau$

Figure 4

// The QGM of an aggregate query that includes having is a triplet ($Q_s$, $Q_g$, $Q_h$):

// $Q_s$ is the SPJ part of $Q$,
// $Q_g$ contains aggregations ranging over $Q_s$, and
// $Q_h$ is a selection over $Q_g$ representing having 1) create an empty QGM for the audit query $AQ$
2) add $Q$ to $AQ$
3) add $A$ to $AQ$
4) rewrite $A$ to additionally range over the result of $Q_s$ with quantifier $x$
5) for each quantifier $r$ in $A$ which is over a table $T$ also in $Q_s$
6) substitute $x$ in place of $r$ in $A$
7) replace the audit list of $A$ with the grouping columns $Q_s$
8) create a new empty select box $B$ and add it to $AQ$
9) add $Q_h$, $A$ as inputs to $B$
10) join inputs of $B$ on grouping columns from $Q_h$ and $A$
11) replace $\Pi(B)$ with id ($Q$)
12) replace every table $T_i$ referenced in $AQ$ with its backlog counterpart $T_i^\tau$ at time $\tau$.

Figure 6

AUDITING COMPLIANCE WITH A HIPPOCRATIC DATABASE

BACKGROUND OF THE INVENTION

1. Field of Invention

The present invention relates generally to the field of managing sensitive data. More specifically, the present invention is related to auditing compliance.

2. Discussion of Prior Art

The requirement for responsibly managing privacy sensitive data is being mandated internationally through legislations and guidelines such as the United States Fair Information Practices Act, the European Union Privacy Directive, the Canadian Standard Association's Model Code for the Protection of Personal Information, the Australian Privacy Amendment Act, the Japanese Personal Information Protection Law, and others. A vision for a Hippocratic database as described in article entitled, "Hippocratic databases" by Agrawal et al., proposes ten privacy principles for managing private data responsibly. A vital principle among these is compliance, which requires auditing disclosures of privacy sensitive information to demonstrate that these disclosures of information adhere to their declared data disclosure policy. Closely related to compliance is the privacy principle of limited disclosure as described in article entitled, "Limiting Disclosure in Hippocratic Databases" by LeFevre et al., which means that the database should not communicate private information outside the database for reasons other than those for which there is consent from the data subject. The principle of limited disclosure comes into play at the time a query is executed against the database, whereas demonstrating compliance is post facto and is concerned with showing that usage of the database indeed observed limited disclosure in every query execution.

Consider Alice who gets a blood test done at Healthco, a company whose privacy policy stipulates that it does not release patient data to external parties without the patient's consent. After some time, Alice starts receiving advertisements for an over-the-counter diabetes test. She suspects that Healthco might have released the information that she is at risk of developing diabetes. The United States Health Insurance Portability and Accountability Act (HIPAA) empowers Alice to demand from Healthco the name of every entity to whom Healthco has disclosed her information. As another example, consider Bob who consented that Healthco can provide his medical data to its affiliates for the purposes of research, provided his personally identifiable information was excluded. Later on, Bob could ask Healthco to show that they indeed did exclude his name, social security number, and address when they provided his medical record to the Cardio Institute. The demand for demonstrating compliance need not only arise from an externally initiated complaint—a company may institute periodic internal audits to proactively guard against potential exposures.

A straightforward approach of physically logging the result set of every query and then using this audit trail to ascertain compliance is unsatisfactory. This approach burdens normal query processing with excessive overhead, particularly for queries that produce a large result set, as every output tuple would cause an additional write to the audit trail. Moreover, the auditing supported by such logging is limited since data disclosed by a query may not be part of the output. For example, P3P as discussed in article entitled, "The platform for privacy preferences 1.0 (P3P1.0) specification" by Cranor et al., allows individuals to specify whether an enterprise can use their data in aggregation. Auditing compliance to such user preferences is not possible given only the log of aggregated results. The above shortcoming might be overcome by logging the tuples read by a query. However, it is non-trivial to determine which out of all the tuples accessed during the processing of a query should be logged.

Oracle offers a "fine-grained auditing" function as described in pages 574-578 of the book entitled, "Oracle Privacy Security Auditing", by Nanda et al., where the administrator can specify that read queries are to be logged if they access specified tables. This function logs various user context data along with the query issued, the time the query was issued, and the other system parameters including the "system change number". Oracle also supports "flash-back queries" as described in pages 613-618 of the book entitled, "Oracle Privacy Security Auditing", by Nanda et al., whereby the state of the database can be reverted to the state implied by a given system change number. A logged query can then be rerun as if the database was in the state to determine what data was revealed when the query was originally run. There does not appear to be any auditing facility whereby an audit expression can be processed to discover which queries disclosed data specified by the audit expression. Instead, Oracle seems to offer the temporal database (flash-back queries) and query logging (fine-grained auditing) components largely independent of each other.

The problem of matching a query against an audit expression bears resemblance to the problem of predicate locking as described in article entitled, "The notions of consistency and predicate locks in a database system" by Eswaran et al., that tests if predicates associated with two lock requests are mutually satisfiable. Besides being expensive, this test can lead to false positives when applied to the auditing problem.

Query processing over views that contain the notion of augmenting a user query with predicates derived from the view definition is discussed in the book entitled "Database Management Systems" by Ramakrishnan et al. Optimizing of a group of queries as described in article entitled "NiagaraCQ: A scalable continuous query system for internet databases" by Chen et al. and article entitled "Multiple-query optimization" by Sellis can be used to accelerate the execution of audit queries.

Article entitled "Computational Issues Connected with the Protection of Sensitive Statistics by Auditing Sum-Queries", by Malvestuto et al., discusses an implementation of an auditing strategy for sum-queries restricted according to a query-set-overlap control. A query map which is a graphical summary of answered queries is used.

Article entitled "The Specification and Enforcement of Advanced Security Policies", by Ryutov et al., discusses an authorization framework that enables the specification and enforcement of advanced policies that can conditionally generate audit records and can react to state generated by intrusion detection engines based on observation of audit records.

U.S. patent assigned to Haystack Labs, Inc. (U.S. Pat. No. 5,557,742), provides an intrusion misuse detection and reporting system that uses processing system inputs, which include processing system audit trail records, system log file data, and system security state data information for further analysis to detect and report processing system intrusions and misuses.

U.S. patent assigned to Hitachi, Ltd. (U.S. Pat. No. 5,982,890), discusses a method and system for detecting fraudulent or unauthorized data update by insiders of databases of a distributed computer system, capable of allowing third parties to check for fraud, by generating parity data of initial data collected from databases and comparing the parity data generated at an auditing time from the latest data stored in the databases with the parity already stored such that if the two do not match, it means that the databases were updated fraudulently.

U.S. patent assigned to The Chase Manhattan Bank (U.S. Pat. No. 6,070,244), discusses an improved security management system for computer systems where deviations from security policies are reported and compliance problems are fixed by administering the native security platforms. The system includes a self-correcting data security audit system. System parameters (e.g. minimum password length made consistent with policy) or user parameters (e.g. forcing a password change at next login) are automatically changed as necessary.

U.S. patent assigned to PRC Inc. (U.S. Pat. No. 6,134,664), discusses a method and apparatus for eliminating audit trail records from further consideration by an intrusion and misuse detection engine. Received identified native audit are compared against at least one template and in case of a match, each of the matched native audits is reduced.

U.S. patent assigned to Psionic Software, Inc. (U.S. Pat. No. 6,405,318 B1), discusses a network independent, host based computer implemented method for detecting intruders in a host computer wherein an unauthorized user attempting to enter into the host computer is detected by comparing actions of the user to a dynamically built profile for the user, and if the action is out of range of the user profile, notifying a control function at the host computer.

U.S. patent application to Kayashima et al. (2001/0025346 A1), provides a security management and audit program database in which information security policy and an object system correspond to management and audit programs.

U.S. patent application assigned to International Business Machines Corporation (2002/0178374 A1), discusses a method and apparatus for protecting data from damage in a data processing system. Detection of a virus may be performed by using pattern matching on system audit trails in which audit trails contain activities occurring within the data processing system.

U.S. patent application assigned to Enterasys Networks, Inc. (2004/0049693 A1), discusses a method for efficiently managing and reporting intrusion, or attempted intrusion events of a computer network using event processing means that detect a corresponding event related to intrusion.

U.S. patent application to Schwartz et al. (2004/0111639 A1), discusses the automatic enforcement of a pre-defined policy, e.g., data access and handling rules developed by network users within a community of trust, regarding sensitive information. A broad range of interactions are monitored to generate alerts and logs that can be reviewed by interested parties to ensure compliance with the established policy.

U.S. patent application to Callahan et al. (2004/0172558 A1), discusses a security repository software that uses a database such that advanced queries can be performed on audit data.

Whatever the precise merits, features, and advantages of the above cited references, none of them achieves or fulfills the purposes of the present invention.

SUMMARY OF THE INVENTION

A method to perform disclosure-based database auditing. At the time of audit, the auditor specifies, using an audit expression, the data whose disclosure is to be tracked by the audit. A subset of logged queries possibly having disclosed the data identified by the audit expression are selected and form the set of candidate queries. These candidate queries are then combined and transformed into an audit query, which when run against the backlog database, identifies the suspicious queries having disclosed the data specified by the audit expression efficiently and precisely.

A system comprising an audit query generator that processes audit expressions specifying the data whose disclosure is to be tracked, is used to perform disclosure-based database auditing. The audit query generator identifies a subset of logged queries from a query log possibly having disclosed the data identified by the audit expression and then formulates an audit query that is run against a backlog database to identify suspicious queries having disclosed the data specified by the audit expression efficiently and precisely.

BRIEF DESCRIPTION OF THE DRAWINGS

FIG. 2 illustrates audit query generation for simple selections, as per the present invention.

FIG. 4 illustrates audit query generation when both the candidate query and the audit query expression contain joins, as per the present invention.

FIG. 6 illustrates audit query generation for an aggregate query containing having clause, as per the present invention.

DESCRIPTION OF THE PREFERRED EMBODIMENTS

Figure 1:
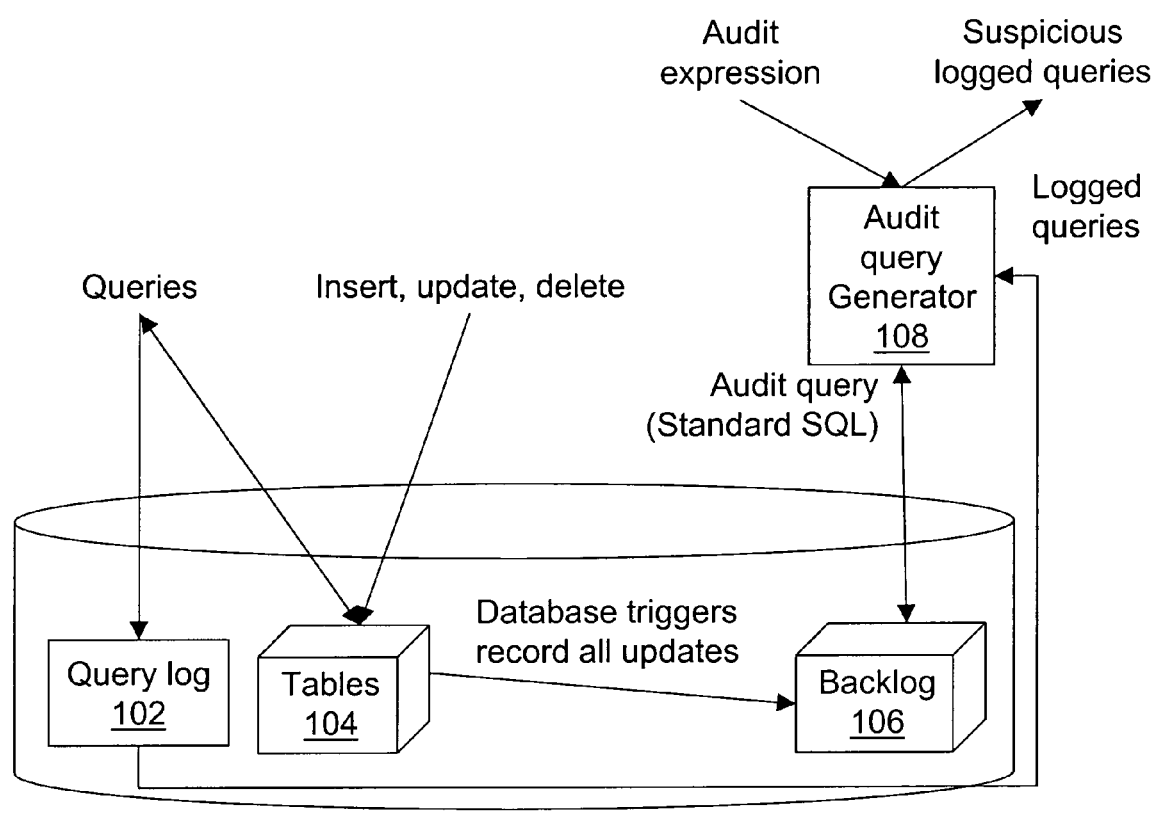
FIG. 1 illustrates an auditing framework, as per the present invention.

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

An ideal audit system should have the following properties:
  Non-disruptive: The system should put minimal burden on normal query processing.
  Fast and precise: The system should be able to quickly and precisely identify all the queries that accessed the specified data.
  Fine-grained: It should be possible to audit even a single field of a specific record.
  Convenient: The language for specifying data of interest should be intuitive and user friendly.

FIG. 1 illustrates an audit system architecture that satisfies the above desiderata. During normal operation, the text of every query processed by the database system is logged along with annotations such as the time when the query was executed, the user submitting the query, and the query's purpose into query log 102. The system uses database triggers to capture and record all updates to base tables 104 into backlog tables of a backlog database 106 for recovering the state of the database at any past point in time. Read queries, which are usually predominant, do not write any tuple to the backlog database.

To perform an audit, an auditor formulates an audit expression that declaratively specifies the data whose disclosure is to be audited (i.e. sensitive data). Sensitive data could be for example, information that a doctor wants to track for a specific individual that could help to resolve disclosure issues during an audit process. Audit expressions are designed to essentially correspond to SQL queries, allowing audits to be performed at the level of an individual cell of a table. The audit expression is processed by an audit query generator 108, which first performs a static analysis of the expression to select a subset of logged queries that could potentially disclose the specified information. It then combines and transforms the selected queries into a single audit query by augmenting them with additional predicates derived from the audit expression. This audit query, expressed in standard SQL, when run against a backlog database 106 yields the precise set of logged queries that accessed the designated data. Indices on the backlog tables make the execution of the audit query fast.

The overhead of the above mentioned approach on query processing is small, involving primarily the logging of each query string along with other minor annotations. Database triggers are used to capture updates in a backlog database. At the time of audit, a static analysis phase selects a subset of logged queries for further analysis. These queries are combined, transformed into an audit query generated as standard SQL, which when run against the backlog database, identifies suspicious queries efficiently and precisely.

Backlog tables of backlog database 106 as shown in FIG. 1 are used to reconstruct the snapshot of the database at the time a logged query was run. Backlog tables are maintained by database triggers which respond to updates over base tables. However, the same backlog organization can instead be computed using DB2 V8 replication services. DB2 V8 uses the database recovery log to maintain table replicas. A special DB2 V8 replication option can create a replica whose organization is similar to backlog tables described above. Thus, using DB2 V8, backlog tables can be maintained asynchronously from the recovery log instead of being maintained using triggers. Oracle offers flash-back queries as yet another alternative to the backlog organization of FIG. 1. A SQL query can be run against any previous snapshot of the database using Oracle SQL language extensions.

Two fundamental assumptions/limitations of the above mentioned system are:

The problem is limited to that of determining if specified data was disclosed by a single query when that query was considered in isolation. There are subtle ways in which an adversary may compose multiple queries to obtain certain information. For example, the statistical database as described in article entitled, "Security-control methods for statistical databases" by Adam at al., discusses how individual information can be deduced by running several aggregate queries and the database security literature as described in article entitled, "Database Security" by Castano et al., shows how covert channels can be used to leak information. The assumption is that end users are not maliciously posing specially crafted queries to deduce information without detection.

The SQL queries considered comprise a single select clause. A large class of queries (including those containing existential subqueries) can be converted into this form as discussed in article entitled, "Extensible/rule based query rewrite optimization in starburst" by Pirahesh et al. Specifically, queries containing selection, projection (including distinct), relational join, and aggregation (including having) operations are considered.

The syntax of an audit expression and the concept of an indispensable tuple which is used to identify suspicious queries with respect to the audit expression can be understood with the help of following definitions:

Definitions

A database D is a collection of base tables. The scheme of table T is denoted as T ($C_0, C_1, \ldots, C_m$) and t.C is used to refer to the value of the field C in tuple t. The following schema will be used in the examples that follow.

Customer (cid, name, address, phone, zip, contact)
Treatment (pcid, date, rcid, did, disease, duration)
Doctor (did, name)

The primary keys have been underlined. A customer can be a patient, someone accepting financial responsibility for a patient's treatment, or an emergency contact. The Treatment table uses pcid to identify the patient receiving the treatment and uses rcid to identify the customer assuming financial responsibility for the treatment (who could be the same person as the patient). The date is the start date of the treatment and duration reflects the length of the treatment. Other column names are self-explanatory. To simplify exposition, it will be assumed that the database has referential integrity and that no field value is null.

Audit Expressions

Expressions that essentially correspond to SQL queries enable an auditor to conveniently specify the queries of interest, termed suspicious queries. Specifically, the syntax of an audit expression is identical to that of a select-project-join (SPJ) query without any distinct in the select list, except that audit replaces the keyword select and the elements of the audit list are restricted to be column names:

audit audit list
from table list
where condition list

Let U be the cross product of all the base tables in the database. The audit expression marks a set of cells in the table U. The marked cells belong to the columns in the audit list for the tuples that satisfy the predicate in the where clause. Queries that access all the marked cells in any of the tuples in U are to be found. These are the suspicious queries with respect to the audit expression.

Example 1: Disclosure of disease information of anyone living in the ZIP code 95120 needs to be audited. Here is the audit expression:

audit disease
from Customer c, Treatment t
where c.cid=t.pcid and c.zip='95120'

This audit expression marks the cells corresponding to the disease column of those tuples in the Customer*Treatment table that have c.cid=t.pcid and c.zip=95120. Any query that accesses the disease column of any of these tuples will be considered suspicious.

Informal Definitions

Indispensable Tuple—ind(t,Q)

A tuple t∈U is indispensable in the computation of a query Q, if its omission makes a difference.

Candidate Query—cand(QA)

A query Q is a candidate query with respect to an audit expression A, if Q accesses all the columns that A specifies in its audit list.

Suspicious Query—susp(Q,A)

A candidate query Q is suspicious with respect to an audit expression A, if Q and A share an indispensable tuple.

Example 2: Consider the audit expression A in Example 1 and the following query Q
select address
from Customer c, Treatment t
where c.cid=t.pcid and t.disease='diabetes'

Q is a candidate query with respect to A as it accesses the disease column that A is auditing. Consider the Customer*Treatment table. Clearly, tuples that match the join condition and have diabetes in the disease column are indispensable for Q. Similarly, tuples that match the join condition and have 95120 as the zip code are indispensable for A. Therefore Q will be deemed suspicious with respect to A if there was some customer who lived in the ZIP code 95120 and was also treated for diabetes.

Example 3: Consider the query Q from Example 2 and the following audit expression A:
audit address
from Customer c, Treatment t
where c.cid=t.pcid and t.disease='cancer'

Q will not be deemed suspicious with respect to A because no tuple in Customer*Treatment can simultaneously satisfy the predicates of Q and A. But how about Alice who has both cancer and diabetes? Although Q discloses Alice's address, the fact that Alice has cancer is not relevant to the query. Q only asks for people who have diabetes. In other words, anyone looking at the output of the query will not learn that Alice has cancer. Hence it is reasonable to not consider the query to be suspicious. Note that all the tuples of Customer*Treatment marked by A have cancer in the disease column and Q does not access any one of them.

Formal Definitions

Let the query Q and audit expression A be of the form:

$$Q=\ldots(\sigma_{P_Q}(T*R)) \quad (1)$$

$$A=\bar{\pi}_{C_{OA}}(\sigma_{P_A}(T*S)) \quad (2)$$

where T, R, S are virtual tables of the database D, that is, cross products of base tables:

$$T=T_1*T_2*\ldots*T_n$$

$$R=R_1*R_2*\ldots*R_m$$

$$S=S_1*S_2*\ldots*S_k$$

The operator $\bar{\pi}$ is the multi-set projection operator that preserves duplicates in the output (as opposed to the relational projection operator $\pi$ which eliminates duplicates). Note that T is common to Q and A. $C_Q$ denotes the column names that appear anywhere in a query Q, and $C_{OQ}$ denotes the column names appearing in the select list of Q. Similarly, $C_{OA}$ denotes the column names present in the audit list of an audit expression A. $P_Q$ denotes the predicate of the query and $P_A$ is the predicate of the audit expression. Tuples of any virtual table are referred to as virtual tuples.

The definition of indispensability, for all classes of queries of interest, specifically (a) SPJ queries, (b) queries with aggregation without having, and (c) queries with aggregation and having, are formalized as follows:

SPJ Queries

Consider first a SPJ query that does not contain a distinct in its select list. Rest of the cases are based on this case. For such queries, the form of the query of Eq. (1) is specialized to:

$$Q=\bar{\pi}_{C_{OQ}}(\sigma_{P_Q}(T*R)) \quad (3)$$

The definition of an indispensable tuple for an SPJ query is formalized as follows:

Definition 1 (Indispensability—SPJ) A (virtual) tuple v∈T is indispensable for an SPJ query Q if the result of Q changes when we delete v:

$$ind(v,Q) \Leftrightarrow \bar{\pi}_{C_Q}(\sigma_{P_Q}(T*R)) \neq \bar{\pi}_{C_Q}(\sigma_{P_Q}((T-\{v\})*R))$$

Theorem 1 A (virtual) tuple v∈T of the SPJ query Q is indispensable if $$ind(v,Q) \Leftrightarrow \sigma_{P_Q}(\{v\}*R) \neq 0 \quad (4)$$

Proof From Definition 1, $$ind(v,Q) \Leftrightarrow \bar{\pi}_{C_Q}(\sigma_{P_Q}(T*R)) \neq \bar{\pi}_{C_Q}(\sigma_{P_Q}((T-\{v\})*R))$$

Since the projections $\bar{\pi}$ maintain the duplicates, $$ind(v,Q) \Leftrightarrow \sigma_{P_Q}(T*R) \neq \sigma_{P_Q}((T-\{v\})*R)$$
$$\Leftrightarrow \sigma_{P_Q}(T*R) \neq \sigma_{P_Q}(T*R) - \sigma_{P_Q}(\{v\})*R)$$
$$\Leftrightarrow \sigma_{P_Q}(\{v\})*R) \neq 0$$

Queries with distinct in the select clause produce a duplicate-free table. Such queries have the form $Q=\pi_{C_{OQ}}(\sigma_{P_Q}(T*R))$. Let Q be the SPJ query obtained from the original query Q after removing distinct from the query text. Then, the definition will be:

Definition 2 (Indispensability—Distinct) A (virtual) tuple V is indispensable for $Q=\pi_{C_{OQ}}(\sigma_{P_Q}(T*R))$ if and only if it is indispensable for $Q'=\bar{\pi}_{C_{OQ}}(\sigma_{P_Q}(T*R))$.

Queries with distinct can be viewed as a special case of aggregation, the aggregation function being the first tuple in a group.

Observation 1 Duplicate elimination does not change the set of indispensable tuples for an SPJ query.

Indispensability—Aggregation Without Having

Consider a query that computes average salary per department. If Alice happens to have exactly the average salary of her department and her tuple is omitted, the query result will not be affected. However, it will be wrong to treat Alice's tuple as dispensable because the privacy systems such as P3P allow individuals to opt out of the use of their values in the computation of an aggregation.

The form of the query of Eq. 1 for an aggregation query without a having clause is specialized to:

$$Q=gby\gamma_{agg}(\sigma_{P_Q}(T*R)) \quad (5)$$

where gby are the grouping columns and agg represent aggregations like avg(duration), count(disease).

Consider the query Q' that is a version of Q, but without aggregations. That is, Q' has exactly the same from and where clauses, and a select clause with the same columns as Q, but without the aggregation functions. Note that the columns used in agg (e.g. duration, disease) are included in the select list of Q'.

Definition 3 (Indispensability—Aggregation) A (virtual) tuple v is indispensable for Q if and only if it is indispensable for the aggregate-free version Q'.

Example 4 Consider the following query that outputs average duration of diabetes treatment by doctor:
select name, avg(duration)

from Doctor d, Treatment t
where d.did=t.did and t.disease='diabetes'
group by name Indispensability of a tuple t in the above query is determined by considering the indispensability of t in the following SPJ query:
select name, duration
from Doctor d, Treatment t
where d.did=t.did and t.disease='diabetes'

Every Treatment tuple having diabetes in the disease field is indispensable. Thus the fact that the duration values of these tuples were used in computing the output is not lost. Thus, the following observation can be made:

Observation 2 A tuple v is indispensable for $Q = gby\ \gamma_{agg}(\sigma_{P_Q}(T*R))$ if and only if it is indispensable for $Q' = \pi_{C_Q}(\sigma_{P_Q}(T*R))$.

Indispensability—Aggregation with Having

Example 5 A modified version of the query given in Example 4 is shown below. It outputs average duration of diabetes treatment, but only for those doctors for whom this average is greater than 100 days.
select name, avg(duration)
from Doctor d, Treatment t
where d.did=t.did and t.disease='diabetes'
group by name
having avg(duration)>100

The general form of an aggregation query Q that includes a having clause can be written as:

$$Q = \sigma_{P_H}(gby\gamma_{agg}(\sigma_{P_Q}(T*R))) \quad (6)$$

Compared to Eq. (5), an extra having predicate $P_H$(avg(duration)>100 in Example 5) is added. Any group that does not satisfy this predicate is not included in the results of Q, which implies that any tuple belonging to a group that gets filtered out by $P_H$ is dispensable. Let Q be the having-free version of Q, obtained by simply removing the having clause from Q.

Definition 4 (Indispensability—Aggregation with having) A (virtual) tuple v is indispensable for Q if and only if it is indispensable for Q and it belongs to a group that satisfies the having predicate $P_H$.

To recast indispensability in terms of an SPJ query, a group table is defined as:

$$G = gby\gamma_{agg}(\sigma_{P_Q}(T*R)) \quad (7)$$

For the example query, G will have two columns: name and avg(duration). it will have as many tuples as there are doctors who treat diabetes. Every tuple will have the average duration of diabetes treatment for the corresponding doctor.

Next form the following table:

$$QG = \sigma_{P_G}((\sigma_{P_Q}(T*R))*G) \quad (8)$$

where $P_G$ is the natural join condition on the group-by-columns, gby. The results tuples of the having-free version Q are augmented with the corresponding group values. The query Q is computed from $\sigma_{P_H}(QG)$.

Observation 3 A (virtual) tuple v is indispensable for query Q with aggregation and having if and only if v is indispensable for the SPJ query $$\pi_{C_Q}(\sigma_{P_H}(\sigma_{P_G}(\sigma_{P_Q}(T*R*G)))) \quad (9)$$

Suspicious Queries

A maximal virtual tuple for queries Q1 and Q2 is defined.

Definition 5 (Maximal Virtual tuple) A tuple v is a maximal virtual tuple for queries and Q1 and Q2, if it belongs to the cross product of common tables in their from clauses.

Definition 6 (Candidate Query) A query Q is a candidate query with respect to the audit expression A if and only if
$$C_Q \supseteq C_{OA}$$

Definition 7 (Suspicious Query) A candidate query Q is suspicious with respect to audit expression A if they share an indispensable maximal virtual tuple v, that is:

$$susp(Q,A) \Leftrightarrow \exists v \in T\ s.t.\ ind(v,Q) \wedge ind(v,A)$$

Note that $T = T_1 * T_2 * \ldots * T_n$ is the cross product of the common tables in Q and A.

System Structures

The system structures needed to handle audits in the presence of updates to the database are as follows:

i) Full Audit Expression

The audit expression is prepended with an additional during clause that specifies the time period of interest:
during start-time to end-time
audit audit-list
...

Only if a query has accessed the data of concern during the specified time period is the query deemed suspicious. Privacy policies specify who is allowed to receive what information and for what purpose as described in article entitled, "Hippocratic databases" by Agrawal et al. and article entitled, "The platform for privacy preferences 1.0 (P3P1.0) specification" by Cranor et al. An audit expression can use the other than clause to specify the purpose-recipient pairs to whom the data disclosure does not constitute non-compliance:
otherthan purpose-recipient pairs
during start-time to end-time
audit audit-list
...

ii) Query Log

As shown in FIG. 1, the audit system maintains a log of past queries executed over the database. The query log is used during the static analysis to limit the set of logged queries that are transformed into an audit query.

A thin middleware lies between the application and the database engine. This middleware is implemented as an extension to a JDBC driver. The middleware intercepts queries and writes the query string and associated annotations to the log. The annotations include the timestamp of when the query finished, the ID of the user issuing the query, and the purpose and the recipient information extracted from the context of the application as described in articles entitled, "Limiting disclosure in Hippocratic databases" by LeFevre et al. and pages 574-578 of the book entitled, "Oracle Privacy Security Auditing", by Nanda et al, in which the query is embedded. The query log is maintained as a table. Some database systems (e.g. DB2) provide the facility for logging incoming queries. This capability can be extended to log additional information required for auditing.

iii) Temporal Extensions

To determine if a candidate query Q accessed the data specified in an audit expression the history is selectively played back. Thus the state of the database as it existed at the time Q was executed needs to be recreated. A backlog database is eminently suited for this purpose.

Two organizations for the backlog database are described: time stamped and interval stamped. In both the organizations, a backlog table $T^b$ is created for every table T in the database. $T^b$ records all updates to T. It is assumed that every table T has a primary key column P; the system can create an internally generated key column otherwise.

Time Stamped Organization

This organization is based on the ideas presented in article entitled, "Incremental implementation model for relational databases with transaction time" by Jensen et al. Aside from all columns in T, a tuple in $T^b$ has two additional columns: TS that stores the time when a tuple is inserted into $T^b$, and OP that takes one of the values from {'insert', 'delete', 'update'}. For every table, three triggers are created to capture updates. An insert trigger responds to inserts in table T by inserting a tuple with identical values into $T^b$ and setting its OP column to 'insert'. An update trigger responds to updates to T by inserting a tuple into $T^b$ having the after values of the tuple in T and setting its OP column to 'update'. A delete trigger responds to deletes in T by inserting into $T^b$ the value of the tuple before the delete operation and setting its OP column to 'delete'. In all the three cases, the value of the TS column for the new tuple is set to the time of the operation.

To recover the state of T at timer $\tau$, the "snapshot" of T at time $\tau$ is generated. This is achieved by defining a view $T^\tau$ over the backlog table $T^b$:

$$T^\tau = \pi_{P,C_1,\ldots,C_m}(\{t | t \in T^b \wedge t.OP \neq \text{'delete'} \wedge \not\exists r \in T^b s.t. t.P = r.P \wedge r.TS \leq \tau \wedge r.TS > t.TS\})$$

The scheme for $T^\tau$ is identical to T. $T^\tau$ contains at most one tuple from $T^b$ for every distinct primary key value P. Among a group of tuples in $T^b$ having an identical primary key value, the selected tuple t is the one that was created at or before time$\tau$, is not a deleted tuple, and there is no other tuple r having the same primary key value that was created at or before time $\tau$ but whose creation time is later than that of t.

Interval Stamped Organization

In this organization, the end time (TE) of a tuple is explicitly stored in addition to the start time (TS). Thus, the combination of TS and TE for a tuple gives the time period during which the tuple was alive. A null value of TE is treated as current time. The operation field (OP) is no longer necessary.

When a new tuple t is inserted into T, the insert trigger also adds t to $T^b$, setting its TE column to null. When a tuple t∈T is updated, the update trigger searches for the tuple b∈$T^b$ such that b.P=t.P∧b.TE=null and sets b.TE to the current time. Additionally, the trigger inserts a copy of t into $T^b$ with updated values and its TE column set to null. When a tuple t is deleted from T, the delete trigger searches for b∈$T^b$ such that b.P=t.P∧b.TE=null and sets b.TE to the current time.

Indexing

Two strategies for indexing a backlog table $T^b$ are:
1. Eager: Index is kept fresh and updated every time $T^b$ is updated.
2. Lazy: Index is created afresh at the time of audit. Otherwise, $T^b$ is kept unindexed.

The advantage of the eager strategy is that there is no latency at the time of audit due to the time needed to build the index. However, an update during normal query processing is burdened with the additional overhead of updating the index. The trade-off is reversed in the lazy strategy.

Columns that need to be indexed are chosen. The primary key can be indexed. A composite index consisting of the primary key concatenated with the timestamp can also be created.

Algorithms

The audit query is generated in two steps:
1. Static Analysis: Select candidate queries (i.e., potentially suspicious queries) from the query log. ("Candidate query" is referred to as a query that passes the static analysis.)
2. Audit Query Generation: Augment every candidate query with information from the audit expression and combine them into an audit query that unions their output to identify the suspicious queries.

Static Analysis

For a given audit expression A, some queries will be judged as non-candidates, and excluded immediately. Four static tests can be utilized for selection of candidate queries. The query log is indexed to make these tests fast.

The first is by comparing the attribute names: with audit columns $C_{OA}$, check whether $C_Q \supseteq C_{OA}$. The second test checks whether the timestamp of query Q is out of range with respect to the audit interval in the during clause of A. The third test checks whether the purpose-recipient pair of Q matches any of the purpose-recipient pairs specified in the other than clause of A. Finally, some queries can be eliminated by checking for contradictions between the predicates $P_Q$ and $P_A$, such as $P_Q$=(age >40) and $P_A$=(age<20). This class of tests is an instance of the constraint satisfaction problem, for which many solution techniques are described in the book entitled "Constant Processing" by Dechter.

Audit Query Generation

At the end of static analysis, a set of candidate queries $Q_i=\{Q_1,\ldots,Q_n\}$ that are potentially suspicious with respect to the audit expression A are found. Every $Q_i$ is augmented with information in A, producing another query $AQ_i$ defined against the view of the backlog database at time $\tau_i$, where $\tau_i$ is the timestamp of $Q_i$ as recorded in the query log. Upon execution of these $AQ_i$ queries, those with non-empty results will comprise the exact set of suspicious queries. However, to increase opportunities for optimization, all $AQ_i$ are combined into one audit query AQ whose output is the union of the output of the individual $AQ_i$. This audit query is the one that is executed against the backlog database.

To simplify exposition, it is assumed that $Q_i$ has only one query Q that is transformed into an audit query AQ. A Query Graph Model (QGM) as discussed in article entitled, "Extensible/rule based query rewrite optimization in starburst" by Pirahesh et al., is used to manipulate Q and A to generate AQ. QGM is an internal representation of queries which captures query semantics and which can be manipulated to transform candidate queries and audit expressions in order to generate an audit query. QGM is composed of entities portrayed as boxes and relationships among entities portrayed as lines between boxes. Entities can be operators among, for example, union, select, group, table. The union operator has multiple inputs having compatible schemas and represents the union of the inputs as a single output stream. The select operator can have multiple inputs and outputs and can be used to express join predicates as well as simple predicates. The group operator has a single input and computes grouping and aggregation. The table operator represents a base table and has a set of columns. Lines between operators represent quantifiers which feed one operator by ranging over the output of another operator. To avoid QGM diagrams from becoming unwieldy, column names are abbreviated. The abbreviated column names used in the figures are indicated in bold letters:
Customer (cid, name, address, phone, zip, contact)
Treatment (pcid, rcid, did, disease, duration, date)
Doctor (did, name)

Simple Selections

Consider first the simple case of a candidate query Q involving a selection over a single base table T and the audit expression A over the same table. This case is a special case of the upcoming SPJ queries.

Lemma 1 Let T be a base table of database D. Let $A=\overline{\pi}_{C_{OA}}(\sigma_{P_A}(T))$ be an audit expression and let $Q=\overline{\pi}_{C_Q}(\sigma_{P_Q}(T))$ be a candidate query. Q is suspicious with respect to A if and only if $\sigma_{P_A}(\sigma_{P_Q}(T)) \neq 0$.

Given that the query Q has passed the static analysis, the combined selection $\sigma_{P_A}(\sigma_{P_Q}(T))$ needs to the checked as whether it is empty or not, which is what FIG. 2 implements using the QGM representation.

The audit query generation algorithm is illustrated using the following example.

Example 6 Candidate query Q: Retrieve all customers in ZIP code 95120.
select*
from Customer
where zip='95120'

Audit expression A: Find queries that have accessed Alice's name and address.
audit name, address
from Customer
where name='Alice'

Figure 3A:
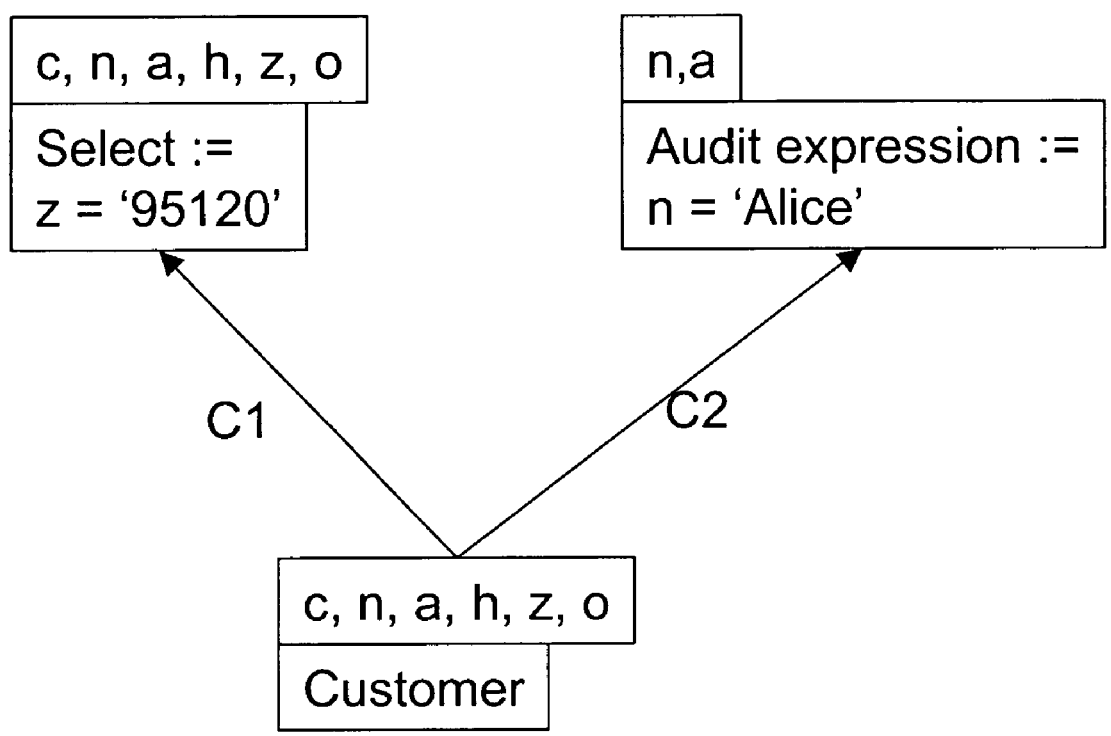
FIGS. 3a and 3b illustrate a QGM for the audit query of example 6, as per the present invention.
Figure 3B:
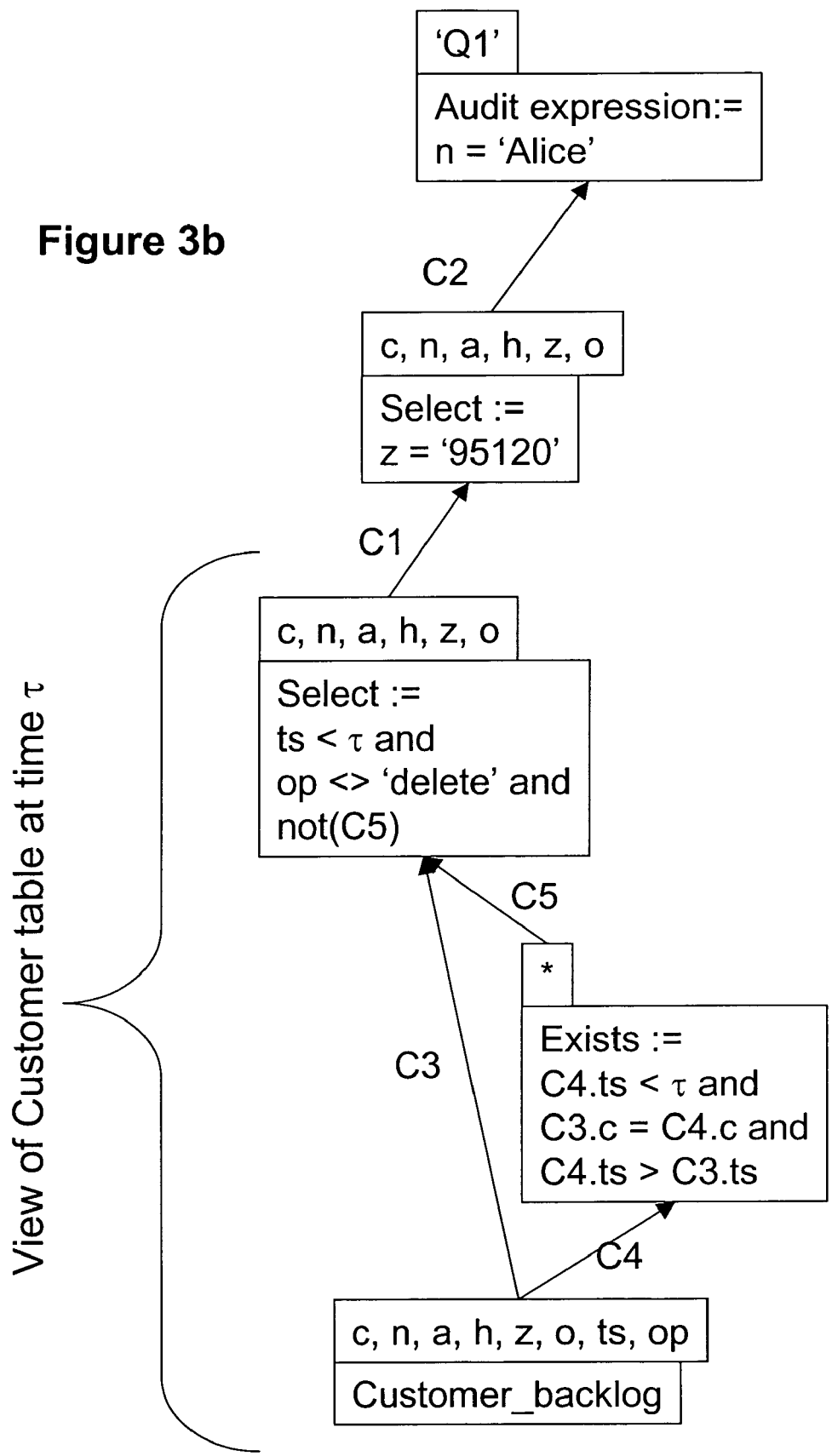

FIG. 3*a* shows the state of the QGM graph after line 3 of FIG. 2. A new QGM structure for the audit query AQ is created and both the candidate query Q and the audit expression are added to AQ. FIG. 3*b* shows the state of QGM after line 6 of FIG. 2. Line 4 of FIG. 2 changed the audit expression's quantifier (range variable) $C_2$ from ranging over the Customer table to ranging over the result of the query Q. As part of this transformation, each column referenced by $C_2$ is changed to reference a column of Q's output. If a column referenced by $C_2$ is not in the output of Q, it is propagated up from the customer table to be included in the Q's select list. Line 5 of FIG. 2 replaces the customer table with a view of the customer table at time τ when Q is completed.

SPJ Queries

Consider now the case when the candidate query as well as the audit expression contain joins in the Where clauses. FIG. 4 shows the audit query generation algorithm when both the candidate query and the audit expression contain joins. The audit list may contain columns from multiple tables and the join condition in the candidate query may be different from the one in the audit expression.

Theorem 2 A candidate SPJ query $Q=\overline{\pi}_{C_Q}(\sigma_{P_Q}(T*R))$ is suspicious with respect to an audit expression $A=\overline{\pi}_{C_{OA}}(\sigma_{P_A}(T*S))$ if and only if $$\sigma_{P_A}(\sigma_{P_Q}(T*R*S)) \neq 0$$

Proof According to definition 7, $$susp(Q, A) \Leftrightarrow \exists m \in T \text{ s.t. } ind(m, Q) \wedge ind(m, A)$$

$$\Leftrightarrow \exists m \in T, r \in R, s \in S \text{ s.t. } P_Q(\{m\ r\}) \wedge P_A(\{m\ s\})$$

-continued $$\Leftrightarrow \exists m \in T, r \in R, s \in S \text{ s.t. } (m\ r\ s) \in \sigma_{P_A}(\sigma_{P_Q}(T*R*S))$$

$$\Leftrightarrow \sigma_{P_A}(\sigma_{P_Q}(T*R*S)) \neq 0$$

Note that an audit expression A may have multiple quantifiers, only some subset of which may range over a table that also appears in query Q. These are the only ones for which A is made to range over the result of the query (lines 5-6 of FIG. 4). For others, A continues to range over the original tables. The following example is used to illustrate the algorithm.

Example 7 Candidate query Q: Find all diseases treated by doctor Phil.
select T.disease
from Treatment T, Doctor D
where T.did=D.did and D.name='Phil'

Audit expression A: Find queries that have disclosed the diseases of Alice.
audit T.disease
from Customer C, Treatment T
where C.cid=T.pcid and C.name='Alice'

Figure 5A:
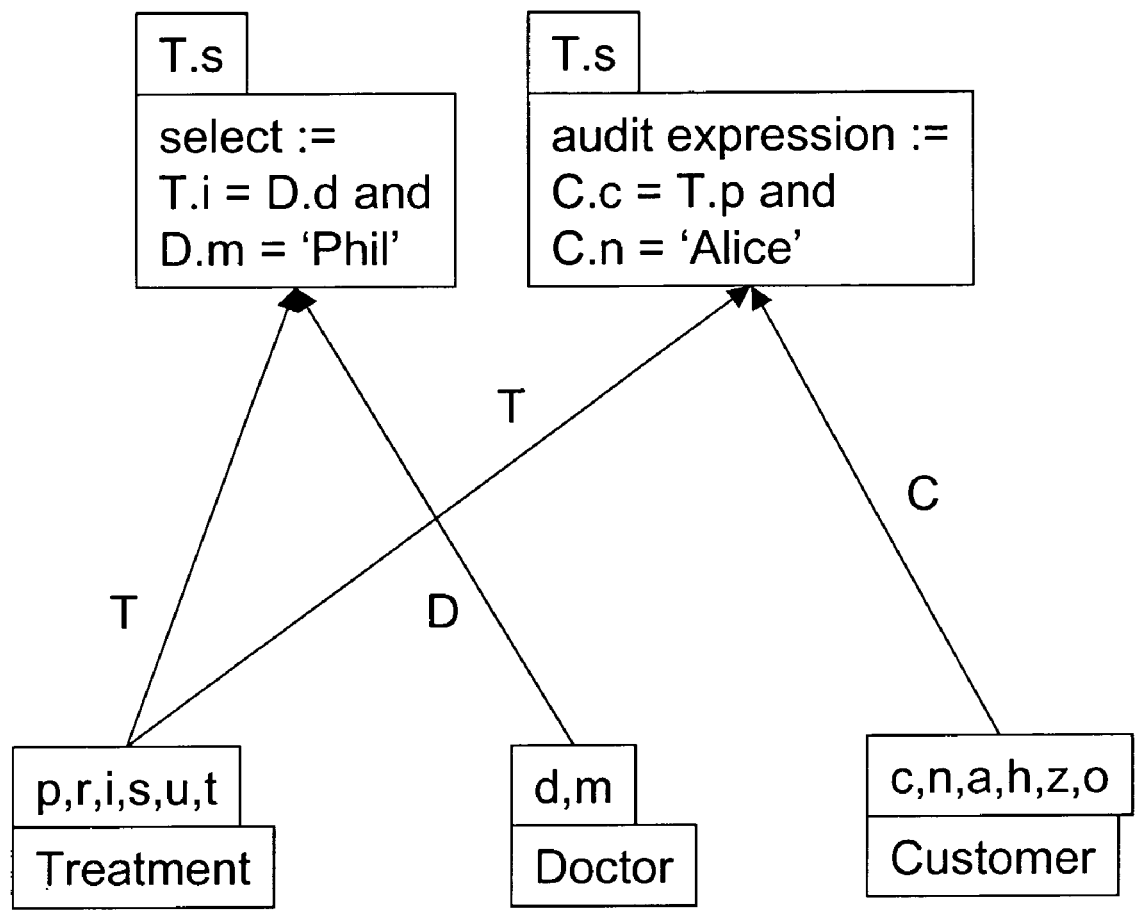
FIGS. 5a and 5b illustrate a QGM for the audit query of example 7, as per the present invention.
Figure 5B:
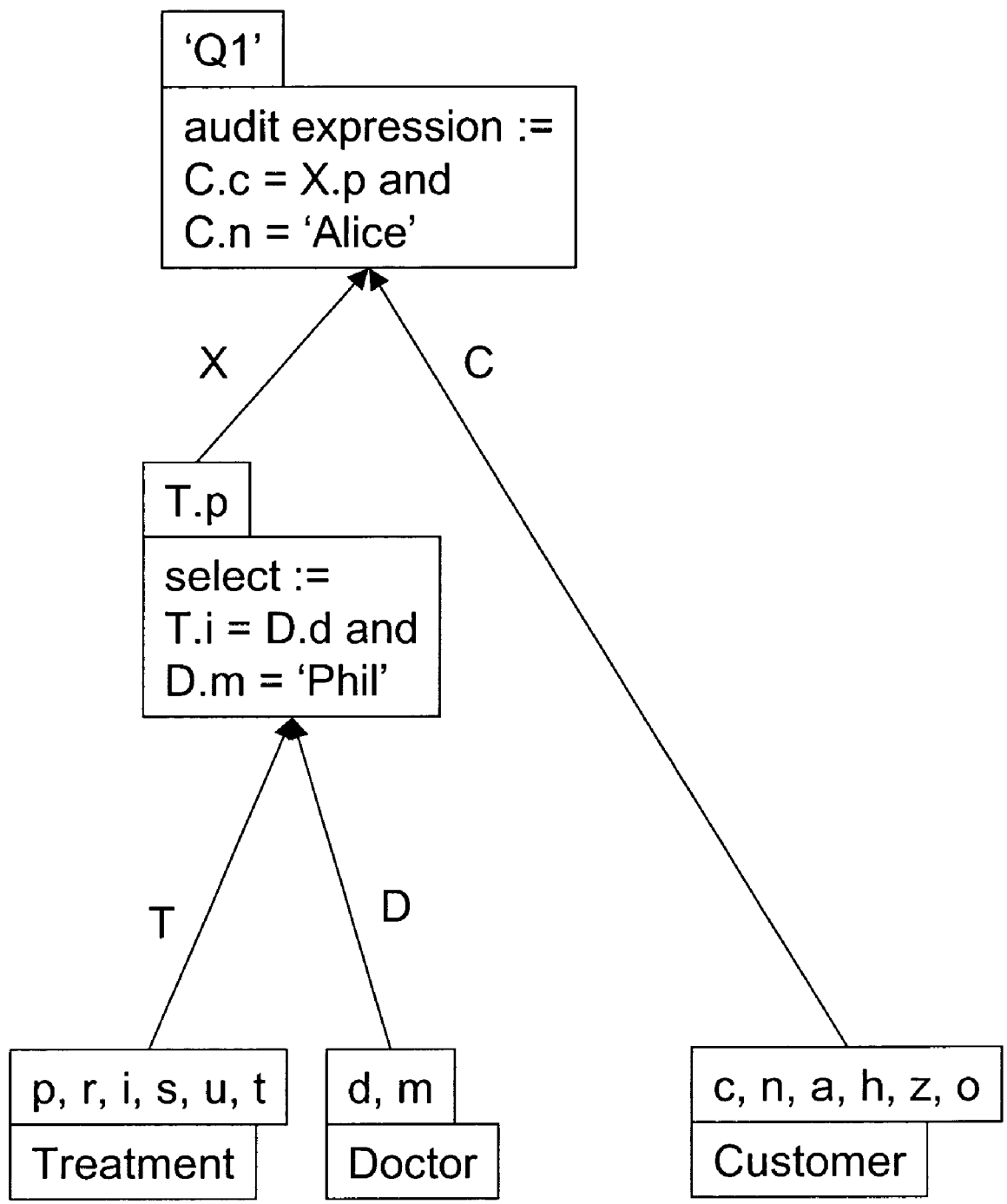

FIG. 5*a* shows the initial QGM (after Line 3 of FIG. 4) and FIG. 5*b* shows the final QGM (after Line 7 of FIG. 4). In the final QGM, the audit expression ranges over the result of the query and then joins the results with the Customer table since Customer only appears in the audit expression.

Aggregation

To determine if an aggregate query without a having clause is suspicious, aggregate functions are simply removed along with the group by clause. Columns previously referenced by aggregate functions are added to the select list of the query. The resulting SPJ query is then handled using the algorithm given in FIG. 4

If the aggregate query, however, additionally contains a having clause, the predicate therein might have eliminated the data specified by the audit expression from the query result. Simply removing the having clause can thus lead to false positives. This limitation is overcome by the algorithm given in FIG. 6, which is based on the upcoming theorem.

Recall that the general form of such a query is given by eq. 6: $Q=\sigma_{P_H}(\text{gby } \gamma_{agg}(\sigma_{P_Q}(T*R)))$. By eq. 7, the group table $G=\text{gby } \gamma_{agg}(\sigma_{P_Q}(T*R))$ and the audit expression is $A=\overline{\pi}_{C_{OA}}(\sigma_{P_A}(T*S))$ by eq. 2.

FIG. 6 shows the audit query generation algorithm for an aggregate query containing having clause.

Theorem 3 A candidate query Q with aggregation and having is suspicious with respect to an audit expression A if and only if $$\sigma_{P_A}(\sigma_{P_H}(\sigma_{P_G}(\sigma_{P_Q}(T*R*G*S)))) \neq 0 \tag{10}$$

Proof From Observation 3, the query Q has the same indispensable tuples as the SPJ query Q' below:

$$Q'=\overline{\pi}_{C_Q}((\sigma_{P_H}(\sigma_{P_G}(\sigma_{P_Q}(T*R*G))))$$

Then, from Theorem 2, Q is suspicious if and only if eq. 10 holds. An aggregate query with a having clause can be viewed as consisting of three parts: $Q_s$, $Q_g$ and $Q_h$. The first part, $Q_s$, ignores grouping and aggregation and finds the tuples qualifying the WHERE clause. Grouping and aggregations are then applied to this result in $Q_g$. Finally, any predicates on groups are applied using a selection operator over the result of grouping and aggregation in $Q_h$. A new select box is created on Line 8 in FIG. 6. This operator joins the tuples emanating from $Q_h$ with those from A to ensure that these A tuples were not all filtered out by the having predicates in $Q_h$. Example 8 is used to illustrate the algorithm in FIG. 6.

Example 8 Candidate query Q: Compute the average treatment duration grouped by disease and the doctor performing the treatment for treatments which were between Jan. 1, 2001 and Dec. 31, 2003 having a minimum duration <100.
select D.name, T.disease, avg(T.duration)
from Doctor D, Treatment T
where T.date between Jan. 1, 2001' and Dec. 31, 2003' and D.did=T.did
group by D.name, T.disease
having min (T.duration)<100

Audit expression A: Find queries that have accessed the disease and treatment duration of patients who have diabetes and live in ZIP code 95120.
audit T.disease, T.duration
from Customer C, Treatment T
where C.cid=T.pcid and C.zip='95120' and T.disease='diabetes'

Figure 7A:
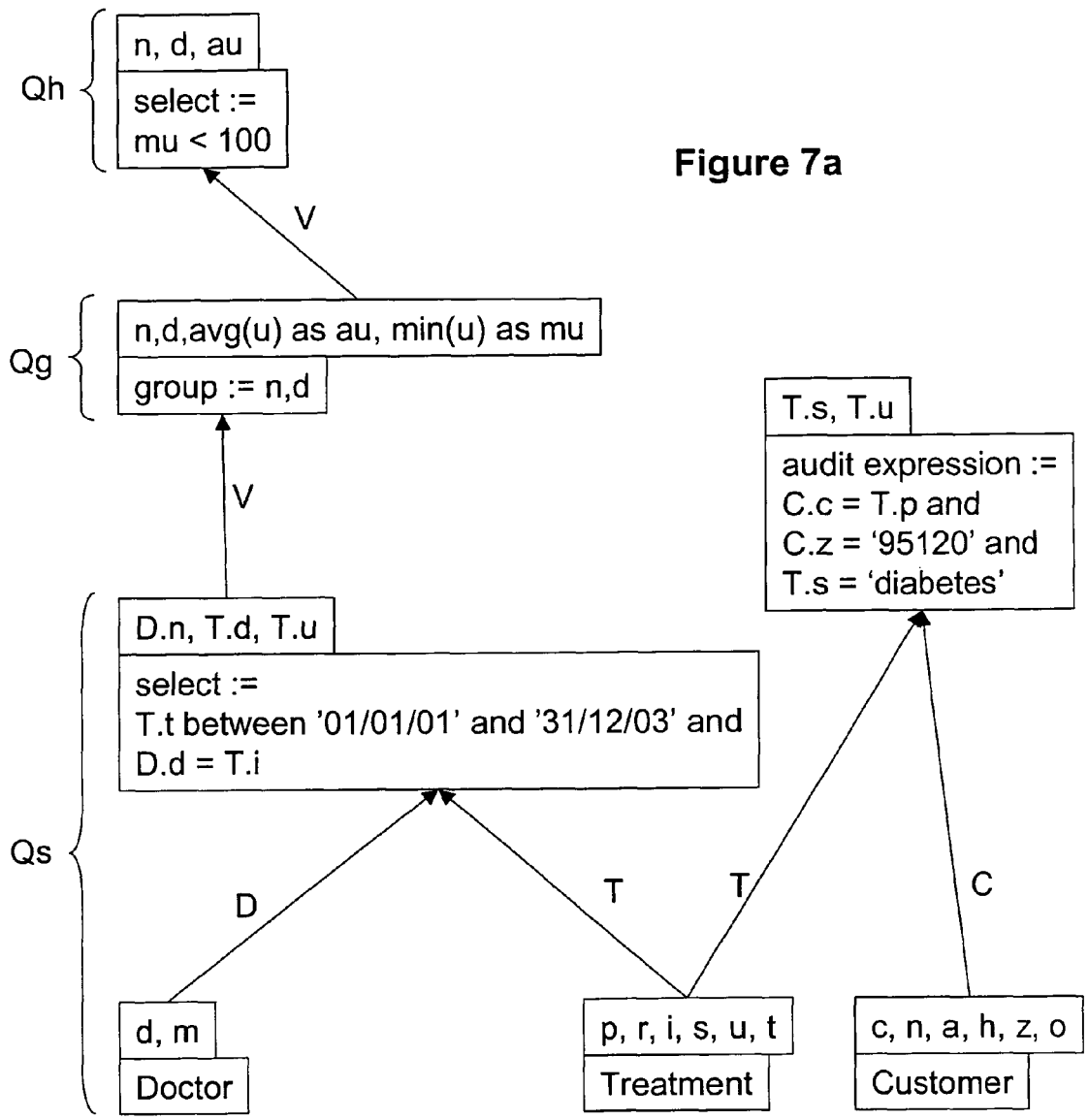
FIGS. 7a and 7b illustrate a QGM for the audit query of example 8, as per the present invention.
Figure 7B:
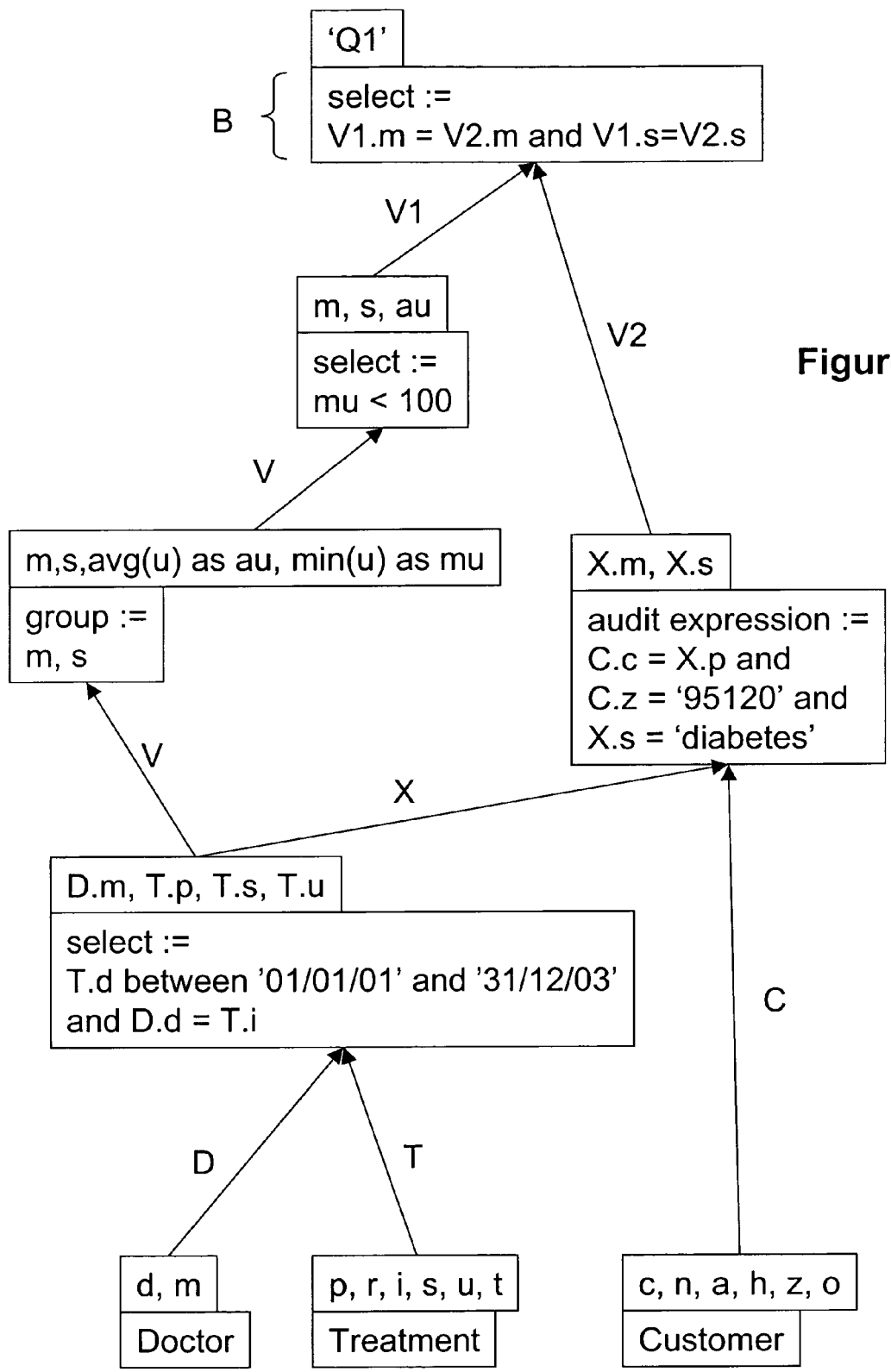

The QGM for the candidate query Q in Example 8 integrated with the audit expression is shown in FIG. 7a. FIG. 7b shows the audit query. The select box B ensures that the groups formed by the grouping operator that survived the having predicate match the audit expression's data.

CONCLUSION

A system and method has been shown in the above embodiments for the effective implementation of an auditing compliance with a hippocratic database. While various preferred embodiments have been shown and described, it will be understood that there is no intent to limit the invention by such disclosure, but rather, it is intended to cover all modifications falling within the spirit and scope of the invention, as defined in the appended claims. For example, the present invention should not be limited by software/program, computing environment, or specific computing hardware.

The above enhancements are implemented in various computing environments. For example, the present invention may be implemented on a conventional IBM PC or equivalent, multi-nodal system (e.g., LAN) or networking system (e.g., Internet, WWW, wireless web). All programming and data related thereto are stored in computer memory, static or dynamic, and may be retrieved by the user in any of: conventional computer storage, display (i.e., CRT) and/or hardcopy (i.e., printed) formats.

The invention claimed is:

1. A computer-based method to perform disclosure-based database auditing, said method comprising:
    formulating one or more audit expressions declaratively specifying sensitive data to be subjected to an audit;
    performing a static analysis of said one or more audit expressions and identifying a subset of logged queries which accessed said sensitive data with respect to said one or more audit expressions;
    formulating a single audit query by combining and transforming said subset of logged queries by augmenting one or more predicates derived from said one or more audit expressions;
    running said audit query against a database to identify suspicious queries that accessed said sensitive data, and outputting said identified queries that accessed said sensitive data.

2. The computer-based method of claim 1, wherein said database records updates made to base tables for recovering the state of said database at a past point in time.

3. The computer-based method of claim 2, wherein said database is rolled back to restore said past point in time which may be when a query was run.

4. The computer-based method of claim 2, wherein backlog tables, DB2 replica tables or Oracle flashback queries are used to recover said state of said database.

5. The computer-based method of claim 1, wherein said logged queries are stored in a query log along with annotations comprising: time when query was executed, user submitting query, and query's purpose.

6. The computer-based method of claim 1, wherein syntax of said audit expression essentially corresponds to a select-project-join (SPJ) SQL query.

7. The computer-based method of claim 1, wherein said audit query is formulated by augmenting each query from said subsets of logged queries with information in said audit expressions.

8. The computer-based method of claim 1, wherein said static analysis comprises any of the following tests: first test for checking whether column names of each of said queries match column names in an audit list of said audit expression; second test for checking if timestamp of each of said queries is out of range with respect to audit interval in the during clause of said audit expression; third step for checking if a purpose-recipient pair of each of said queries matches any of purpose-recipient pairs specified in an otherthan clause of said audit expression; and fourth step for checking contradictions between predicates of each of said queries and said audit expression.

9. A system to perform disclosure-based database auditing, said system comprising:
    a query log storing one or more queries submitted to said system along with annotations;
    a database capturing and recording updates to base tables;
    an audit query generator processing one or more audit expressions declaratively specifying sensitive data to be subjected to audit, said audit query generator performing a static analysis of said one or more audit expressions and identifying a subset of logged queries from said query log which accessed said sensitive data with respect to said one or more audit expressions, formulating a single audit query by combining and transforming said subset of logged queries by augmenting one or more predicates derived from said one or more audit expressions; running said audit query against said database to identify suspicious queries that accessed said sensitive data, and outputting said identified queries that accessed said sensitive data.

10. The system of claim 9, wherein said database records said updates for recovering the state of said database at a past point in time.

11. The system of claim 10, wherein said database is rolled back to restore said past point in time which may be when a query was run.

12. The system of claim 10, wherein backlog tables, DB2 replica tables or Oracle flashback queries are used to recover said state of said database.

13. The system of claim 9, wherein said annotations comprise, time when query was executed, user submitting query, and query's purpose.

14. The system of claim 9, wherein syntax of said audit expression essentially corresponds to a select-project-join (SPJ) SQL query.

15. The system of claim 9, wherein said audit query is formulated by augmenting each query from said subset of logged queries with information in said audit expressions.

16. The system of claim 9, wherein said static analysis comprises any of the following tests: first test for checking whether column names of each of said queries match column names in an audit list of said audit expression; second test for checking if timestamp of each of said queries is out of range with respect to audit interval in the during clause of said audit expression; third step for checking if a purpose-recipient pair of each of said queries matches any of purpose-recipient pairs specified in an otherthan clause of said audit expression; and fourth step for checking contradictions between predicates of each of said queries and said audit expression.

17. An article of manufacture having computer usable medium storing computer readable program code implementing a computer-based method to perform disclosure-based database auditing, said medium comprising:

computer readable program code formulating one or more audit expressions declaratively specifying sensitive data to be subjected to an audit;

computer readable program code performing a static analysis of said one or more audit expressions and identifying a subset of logged queries which accessed said sensitive data with respect to said one or more audit expressions;

computer readable program code formulating a single audit query by combining and transforming said subset of logged queries by augmenting one or more predicates derived from said one or more audit expressions;

computer readable program code running said audit query against a database to identify suspicious queries that accessed said sensitive data, and computer readable program code outputting said identified queries that accessed said sensitive data.

18. The article of manufacture of claim 17, wherein said medium further comprises computer readable program code performing said static analysis comprises executing any of the following tests: first test for checking whether column names of each of said queries match column names in an audit list of said audit expression; second test for checking if timestamp of each of said queries is out of range with respect to audit interval in the during clause of said audit expression; third step for checking if a purpose-recipient pair of each of said queries matches any of purpose-recipient pairs specified in an otherthan clause of said audit expression; and fourth step for checking contradictions between predicates of each of said queries and said audit expression.

* * * * *